United States Patent [19]
Armistead

[11] Patent Number: 5,838,759
[45] Date of Patent: Nov. 17, 1998

[54] SINGLE BEAM PHOTONEUTRON PROBE AND X-RAY IMAGING SYSTEM FOR CONTRABAND DETECTION AND IDENTIFICATION

[75] Inventor: Robert A. Armistead, Los Altos Hills, Calif.

[73] Assignee: Advanced Research and Applications Corporation, Sunnyvale, Calif.

[21] Appl. No.: 869,318

[22] Filed: Jun. 5, 1997

Related U.S. Application Data

[63] Continuation-in-part of Ser. No. 674,919, Jul. 3, 1996, Pat. No. 5,638,420.
[51] Int. Cl.[6] .................................................. G01N 23/04
[52] U.S. Cl. .............................................. 378/57; 378/62
[58] Field of Search .......................................... 378/57, 62

[56] References Cited

U.S. PATENT DOCUMENTS

| | | | |
|---|---|---|---|
| 5,098,640 | 3/1992 | Gozani et al. | 376/166 |
| 5,638,420 | 6/1997 | Armistead | 378/57 |

OTHER PUBLICATIONS

J. L. Jones et al., "Pulsed photon interrogation with neutron-induced gamma-ray spectrometry for cargo inspections", *Proc. SPIE*, vol. 2276 Cargo Inspection Technologies, pp. 326–338 (1994).

*Primary Examiner*—Craig E. Church
*Attorney, Agent, or Firm*—Thomas Schneck

[57] ABSTRACT

An inspection system for detecting contraband in cargo containers, vehicles, rail cars, etc. having an X-ray source and X-ray imaging capability. A cargo container or vehicle is scanned with the beam to look for possible target objects, such as contraband. If the X-ray image shows the existence of targets or possible targets at specific sites, each site may be probed with neutrons by placing a beam converter plate in front of the same X-ray beam used for X-ray imaging, converting the beam to a neutron beam. The neutrons are quickly thermalized and captured by materials producing nuclear reactions with specific elements, yielding gamma rays whose energy is characteristic of particular specific elements. For special nuclear materials, the neutron probe beam can induce the emission of fission neutrons which can be detected. Disclosed are embodiments where the cargo container is fixed and the X-ray equipment is mobile and where the cargo container is mobile and the X-ray equipment is fixed.

15 Claims, 4 Drawing Sheets

SINGLE BEAM PHOTONEUTRON PROBE AND X-RAY IMAGING SYSTEM FOR CONTRABAND DETECTION AND IDENTIFICATION

CROSS-REFERENCE TO RELATED APPLICATION

This is a continuation-in-part of application Ser. No. 08/674,919, filed Jul. 3, 1996, now U.S. Pat. No. 5,638,420.

TECHNICAL FIELD

The invention relates to an inspection method which combines X-ray imaging and photoneutron probing for detecting contraband and verifying manifests in large objects such as international shipping containers, vehicles and rail cars.

BACKGROUND OF INVENTION

X-ray imaging is considered to be one of the most practical approaches for detecting contraband within air and sea cargo containers, vehicles and rail cars. U.S. Pat. No. 5,638,420, assigned to the assignee of the present invention, is an example of such a system. However, although X-ray inspection can generally verify manifests and definitively detect some types of stolen objects (e.g. automobiles), X-ray imaging does not specifically identify the presence of such contraband as drugs, explosives or special nuclear materials. Thus, such contraband is inferred mainly through detecting hidden compartments and "suspicious" masses.

Although neutron techniques have not proven to be practical for providing images of the contents of such objects, they have the ability to specifically identify certain important types of contraband such as drugs, explosives and nuclear materials. Neutron activation followed by gamma-ray spectroscopy has been employed for nondestructive material identification for several decades. First performed with neutrons from nuclear reactors, more recent approaches have used isotopic sources (Am—Be, 252 Cf) or accelerator-type neutron generators employing deuterium/deuterium and deuterium/tritium reactions. A neutron impinging on an object can initiate several types of nuclear reactions with its constituent elements. In many cases, gamma rays are emitted with characteristic and distinct energies. These gamma rays are like the "fingerprints" of the elements in the object. By counting the number of gamma rays emitted with a given energy, the presence and amount of the elements within the object can be deduced. For contraband detection, the measurements focus on specific elements. For example, for thermal neutron analysis (TNA), contraband is detected by the measurement of an anomalously high nitrogen signature (for many explosives) and of an anomalously high chlorine signature (for cocaine and heroin which are typically smuggled as chlorides); for pulsed fast neutron analysis (PFNA), detection is accomplished by measuring key elemental ratios.

In an article by J. L. Jones et. al., entitled "Pulsed Photon Interrogation with Neutron-induced Gamma-ray Spectrometry for Cargo Inspections", in Cargo Inspection Technologies, A. H. Lawrence, ed., Proc. SPIE 2276, pp. 326–338 (1994), the authors disclose a somewhat related technique using beams of pulsed X rays to produce pulsed photoneutrons. A high-energy (>8 MeV) electron accelerator is used to generate X rays which are directed at the object to be inspected. Direct interactions with the inspected materials will produce photoneutrons and/or photofission neutrons in nuclear materials. These neutrons, when captured by a material, can induce the emission of a gamma ray. A measurement of the gamma-ray energies and intensities will reveal the presence and amount of certain types of contraband.

Although research involving neutron methods for inspecting cargo has been ongoing for many years and prototype systems assembled, there are problems in using neutron-based systems for inspecting large objects such as sea cargo containers and vehicles. The problems include: a large hardware footprint and weight (for accelerator sources), overall cost, short source lifetime (for isotopic sources), the high attenuation of neutrons by water and substances containing water (vegetable and fruits), and very low inspection throughput. There are also safety issues related to the handling of radioactive sources or, when subjecting the entire container to a high-intensity neutron irradiation, dealing with the induced activity of inspected materials, especially steel, which is the primary material used for containers and vehicles. Overall, U.S. Customs Service experts have concluded that the risks presented by the deployment of such neutron-based inspection systems far outweigh the benefits.

In U.S. Pat. No. 5,098,640, T. Gozani et. al. disclose a dual-stage inspection system involving an X-ray inspection stage and a second fast neutron inspection stage. By using two separate sources and detectors, the inventors claim a higher probability of detecting specified contraband than if only the X-ray method or the neutron method is used. The use of two separate inspection stations presents major cost and space issues.

An object of the present invention is to improve upon the ability to rapidly identify possible contraband in large containers and then attempt a high probability confirmation using related compact, cost-effective apparatus.

SUMMARY OF INVENTION

The above objective has been met with a cargo inspection system which uses a single beam for a unique combination of X-ray inspection and neutron-induced gamma-ray spectroscopy employing a "photoneutron probe". The X-ray inspection system uses a commercial linear accelerator X-ray source; a variety are available with peak accelerating energies from 2 MV to 15 MV. The X rays are emitted in a continuous string of pulses. Such X-ray sources are reasonably compact and inexpensive compared to accelerator-type neutron sources. For probing suspicious masses or areas of vehicles and containers detected in the X-ray image, the same X-ray beam source is temporarily converted to a pulsed source of neutrons by inserting a beryllium (Be) sheet, i.e., a beam converter, in the X-ray beam. The interaction of X rays with the Be converter can generate photoneutrons. The difference between the parent X-ray energy and the photoneutron reaction threshold energy is available to the neutron as kinetic energy. The neutron yield cross-sections for photoneutron interactions are well documented.

In this invention, the inspection process is a two-tiered approach. First, the contents of a vehicle or container are inspected using X-ray imaging in a scanning mode. If nothing unusual is detected, the object is cleared. However, if suspicious shapes, densities or compartments are revealed, the X-ray source would temporarily be converted into a neutron source using a Be converter to produce a pulsed beam of photoneutrons targeted on designated suspicious areas. Contraband, if present, would absorb thermalized neutrons and emit gamma rays (or, in the case of special nuclear materials, fission neutrons) characteristic of the material of interest. A threat is revealed if gamma rays characteristic of nitrogen, in the case of many explosives and "fertilizer bombs," or chlorine, in the case of certain drugs such as heroin and cocaine typically smuggled as chlorides, are detected. Likewise, special nuclear materials (e.g., uranium and plutonium) can be detected by fission neutrons produced by capture of the photoneutrons.

During photoneutron probing, the inspected item is bathed in a pulsed beam of neutrons. The neutrons lose energy as they scatter, and this continues until they have reached thermal energies. This usually takes less than one microsecond. Once thermalized, neutrons either leak away or are absorbed. This process occurs over time on the order of hundreds of microseconds. The neutron absorption is often followed by the emission of gamma rays with very specific energies or fission neutrons in the case of special nuclear materials. The spectrum of these gamma rays (or neutrons) can be analyzed to detect the presence of various elements. Nitrogen and chlorine are among the elements for which this technique is partially sensitive since they emit copious quantities of gamma rays after thermal neutron absorption. Furthermore, these gamma rays are high in energy relative to most of the gamma rays emitted during neutron absorption by other nuclei. Consequently, background signals and false calls should be relatively small. With this type of neutron probing, it is not necessary to precisely align the beam with the targeted area since the multiple scattering of neutrons during thermalization result in the coverage of a relatively extended area.

The minimum detection limit (MDL) is a function of the X-ray beam energy spectrum, the X-ray beam intensity, and the type and bulk density of the cargo. In general, the MDL will be lower in empty or lightly-loaded trucks, somewhat higher in metal cargoes, and higher still in full-loaded organic cargoes, such as grain or plastic.

The design of the gamma-ray detection system must insure that it is primarily sensitive to those gamma rays which are emitted by thermal neutron absorption. There is a very large background in the gamma-ray detectors during the period when the "X-ray flash" strikes the Be target.

Therefore, it is necessary to carefully shield the detectors and to gate the data acquisition so that this background is reduced to a level that does not obscure the signal. There are several standard techniques for performing this gating so that even with the large X-ray flash, the detection system recovers between a few microseconds to tens of microseconds. This recovery is sufficient to measure the thermal neutron capture signals. There are a variety of organic and inorganic (plastic) gamma-ray detectors that can be used.

This invention, which employs both X-ray imaging and a photoneutron probe, offers substantial advantages over both standard X-ray inspection techniques and the various types of neutron inspection techniques that are being evaluated. Furthermore, these advantages are received at a relatively modest additional cost since the same mechanical apparatus, the same source, and much of the same data acquisition and analysis hardware is used for both X-ray imaging and photoneutron probing.

BEST MODE OF CARRYING OUT THE INVENTION

Figure 1:
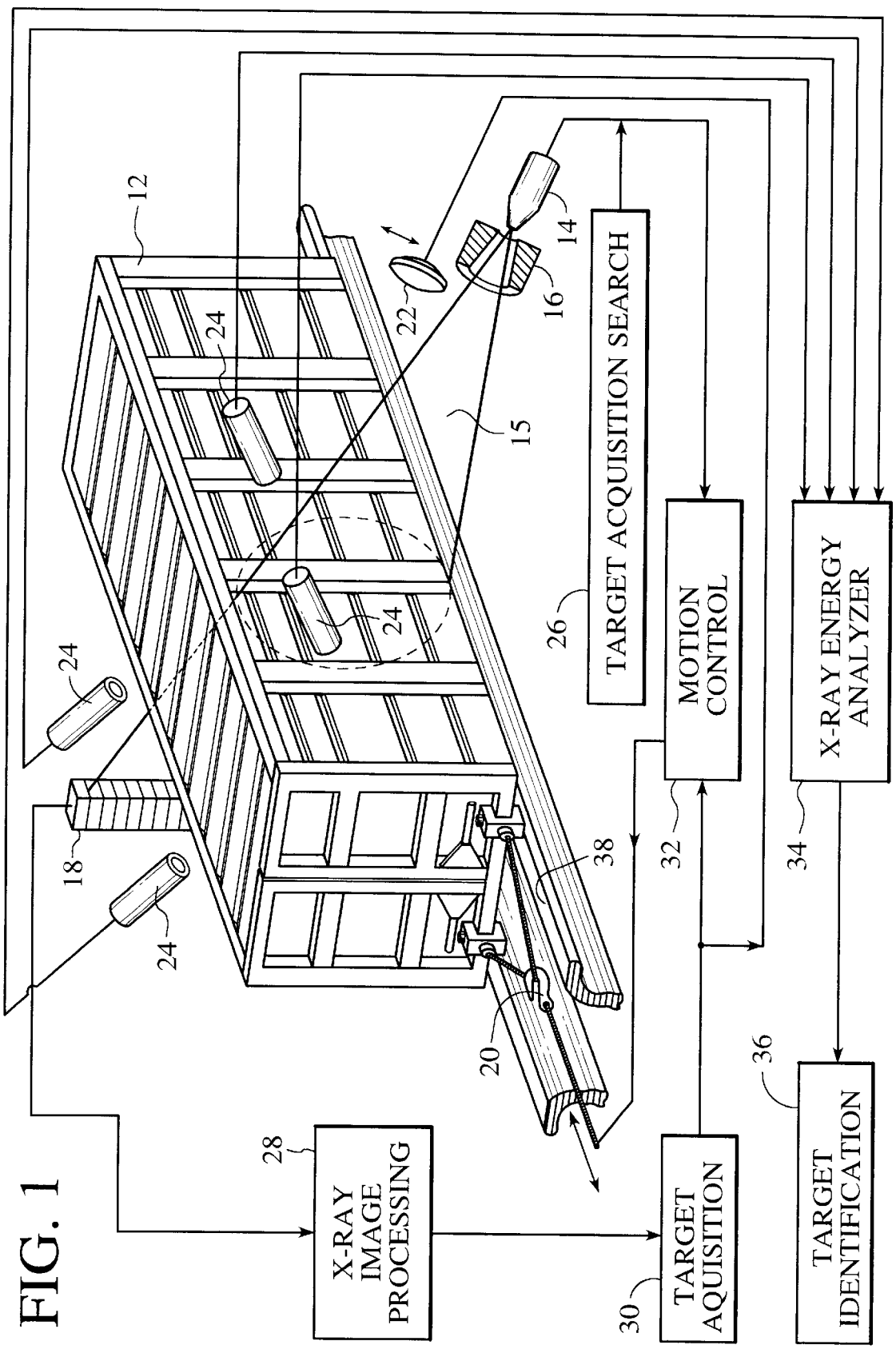
FIG. 1 is a plan view of a fixed inspection system of the present invention probing a movable shipping container.

With reference to FIG. 1, a closed ocean-going cargo container 12 is seen being pulled along a conveyor 38 by a towing hook 20 into an inspection system of the present invention. Such containers are usually made of corrugated steel or aluminum. Other shipping containers, such as air freight cargo boxes, may be similarly arranged for inspection.

An X-ray source 14 generates a fan-shaped or conical X-ray beam 15 which is shaped by a collimator 16 and directed toward a detector array 18 as soon as the container trips a sensor, not shown, which marks the boundary of the inspection system with a signal generated in target acquisition search electronics 26, a start-stop switch. The X-ray source 14 is a commercially available linear accelerator having an energy in the range of 2 to 15 MeV. Since only photons above the approximately 1.67 MeV threshold in beryllium can produce photoneutrons, the higher the energy of the X-ray source, for example, from a linear accelerator, i.e., "linac", the greater the intensity of the photoneutrons. Commercial linacs are available with peak accelerating voltages of 2 MeV, 4 MeV, 6 MeV, 9 MeV and 15 MeV and, on special order, at other energies. For mobile cargo inspection systems operating in congested port facilities, to promote safety, it is desirable to operate at as low an X-ray energy as possible.

However, the X-ray flux must be sufficient to traverse the container 12 and the intensity of generated photoneutrons increases rapidly as the accelerating voltage is increased. Thus, the best X-ray source would be a linac that can be switched between low-energy and high-energy operation. Commercial linac X-ray sources are available that can be switched between approximately 2 and 6 MeV; 6, 9 and 11 MeV; and 9 and 15 MeV. Using a switchable X-ray source, the cargo would be initially inspected by X-ray imaging at the low-energy setting; if the cargo showed areas of sufficiently high density to prevent a good image, the high-energy setting could be used to increase the X-ray flux and reduce the attenuation on those areas.

The X-ray detector array 18 may be formed by a stack of crystals which generate analog signals when X rays impinge upon them, with the signal strength inversely proportional to the amount of beam attenuation in the container. The preferred X-ray beam detector arrangement consists of a linear array of solid-state detectors of the crystal-diode type. A typical arrangement uses cadmium tungstate scintillating crystals to absorb the X rays transmitted through the object being inspected and to convert the absorbed X rays into photons of visible light. There are alternative crystals such as bismuth germinate and sodium iodide. The crystals can be directly coupled to a suitable detector, such as a photodiode or photomultiplier; however, it is preferred to use optical light pipes to carry the light to the detectors along a path at a sharp angle to the X-ray beam so that the detectors can be shielded from the direct X rays and from most of the scattered X rays. The preferred detectors are a linear arrangement of photodiodes, which though unity-gain devices, provide advantages over photomultiplier detectors in terms of operating range, linearity and detector-to-detector matching. An area detector is an alternative to linear array detectors. Such an area detector could be a scintillating strip, such as cesium iodide or other, viewed by a suitable camera or optically coupled to a charge-coupled device (CCD). When a CCD is used, light pipes map the light from the linear scintillator onto discrete areas of the CCD. In the computer, the signals from the area detector are remapped back to a linear column of data and stored in memory. As the beam and detectors move with the straddle vehicle, a two-dimensional image is formed by the concatenation of individual columns over the time necessary for the straddle vehicle to pass over the container or other object being inspected.

For high-resolution applications, the electronics used to read out the detector signals typically feature auto-zeroed, double-correlated sampling to achieve ultra-stable zero drift and low-offset-noise data acquisition. Automatic gain ranging may be used to accommodate the wide attenuation ranges that can be encountered with large containers and vehicles.

At any point in time when the source is on, the detector stack 18 is a snapshot of X-ray beam attenuation in the container for a particular "slice" of the container. Each slice is a beam density measurement, where the density depends upon X-ray beam attenuation through the container. The X-ray source 14 is pulsed in synchronism with gating of the detector stack and motion of the container through the system to obtain representative slices giving a picture of the contents of the container. The resolution of the picture depends upon characteristics of the X-ray source, the number and size of detector cells in the detector array 18, as well as the snapshot rate as the container moves past the beam.

X-ray image processing electronics 28 constitute a computer and semiconductor memory which records the detector snapshots and software to stitch them together to form an X-ray image of the container which may be plotted on a screen or on other media. The X-ray image is viewed or automatically analyzed by target acquisition electronics 30. In the simplest case, the target acquisition electronics may be a CRT or monitor which displays the X-ray image of the container to an operator. Alternatively, the target acquisition electronics 30 may be a database of X-ray images of desired targets, such as automobiles, bricks or other shapes which can be compared with features in the image. Once a target is identified, a signal is sent to the motion control electronics 32 which causes the conveyor 38 or movable inspection system to move back so that a particular target is in the path of beam 15. Now, however, a signal is also sent to an actuator, not shown, associated with converter plate 22, which is interposed in the path of the X-ray beam. The converter plate is a foil, sheet or block which receives X rays and, by means of one or more nuclear reactions, liberates neutrons. The impingement of X rays on beryllium is a well known approach for converting an X-ray beam to a beam of neutrons which become thermalized after scattering interaction with the cargo in a time on the order of one microsecond. Be9 is converted to Be8 and a neutron emitted upon impingement of a gamma ray above the threshold energy of 1.67 Mev for the photoneutron reaction. Since the X-ray source 14 is rated with a peak accelerating potential of at least 2 MeV, X rays with energies greater than the threshold energy will be available to generate photoneutrons.

Neutrons penetrating the container 12 are thermalized or slowed by several mechanisms, including inelastic and elastic scattering. Thermal neutrons can be absorbed by certain elements which may then give off gamma rays of characteristic energy. Such gamma rays are given off in random directions. Gamma ray detectors 24 are disposed to sample the characteristic gamma rays. An analysis of the energy of these gamma rays can be used to detect the presence and amounts of various elements. There are several types of readily available detectors, each with its own set of attributes, that can be used. A primary candidate is a thallium-doped sodium iodide (NaI[T1]) scintillator coupled to a photomultiplier tube. Such detectors are relatively inexpensive, readily available, and have good gamma-ray spectroscopy characteristics; they do, however, have a possible difficulty with the buildup of "afterglow" from the X-ray photons which can impact data collection. An alternative is a bismuth germanate (BGO) detector. These detectors have a significantly smaller problem from afterglow; however, they are more expensive than NaI(T1) scintillators and have inferior gamma-ray spectroscopy characteristics. High-purity germanium (HPGe) detectors provide superior energy resolution, but are much more expensive and require cooling. Also, the energy resolution provided by HPGe detectors would be useful for applications involving an analysis of all of the elements present in cargo for the purpose of verifying manifests; it is not required for the measurement of the chlorine or nitrogen gamma rays emitted after thermal neutron capture.

For the high-sensitivity detection of contraband, the placement and shielding of the detectors as well as the design of the associated data acquisition electronics are important considerations. In particular, it is important that the gamma-ray detection system only be sensitive to those gamma rays which are emitted by thermal neutron absorption. There will be a very large background in the gamma-ray detectors during the period when the "X-ray flash" strikes the Be target. To mitigate the absorption of X-rays, the detectors 24 should be placed out of the direct X-ray beam. A primary position is on the same side of the object as the source, and above and below if structurally possible. It is important to carefully shield the detectors and to gate the data acquisition so that this background is reduced to a level that does not obscure the signal. There are several standard techniques for performing this gating, so that even with the large X-ray flash, the detection system recovers between a few microseconds to tens of microseconds. This recovery is sufficient to measure the delayed thermal-neutron-capture signals.

In a sense, the neutron beam produces gamma ray fluorescence from neutron activation of specific atoms. The output signal from the energy-dependent detectors 24 provides information about the type and amount of materials that are present, i.e., the gamma-ray energy identifies the material, the relative count rate is related to the quantity of that material. The signal is transmitted to an energy analyzer 34, essentially a spectrometer, which is looking for energy peaks characteristic of neutron interactions with particular atoms. Nitrogen (found in nitrogen-based explosives) and chlorine (found in drug chlorides) give off characteristic gamma rays. The target identification electronics 36 associates the energy found in the gamma-ray energy analyzer 34 with particular target substances and counts the number of sample signals. From the sample, a statistical projection is made regarding whether actual contraband exists and an output display 36 registers the target identification. In a similar manner, the neutron probe beam can be used to detect special nuclear materials by inducing the emission of fission neutrons which are detected and analyzed.

Motion control device 32, which includes a motor, causes the container 12 (or possibly a vehicle) to be scanned through an X-ray inspection station on a first pass. After processing the X-ray image, if indications of possible contraband are found, the motion control device 32 transports the container back to a position where neutron activation is appropriate. The process may be repeated.

Figure 2:
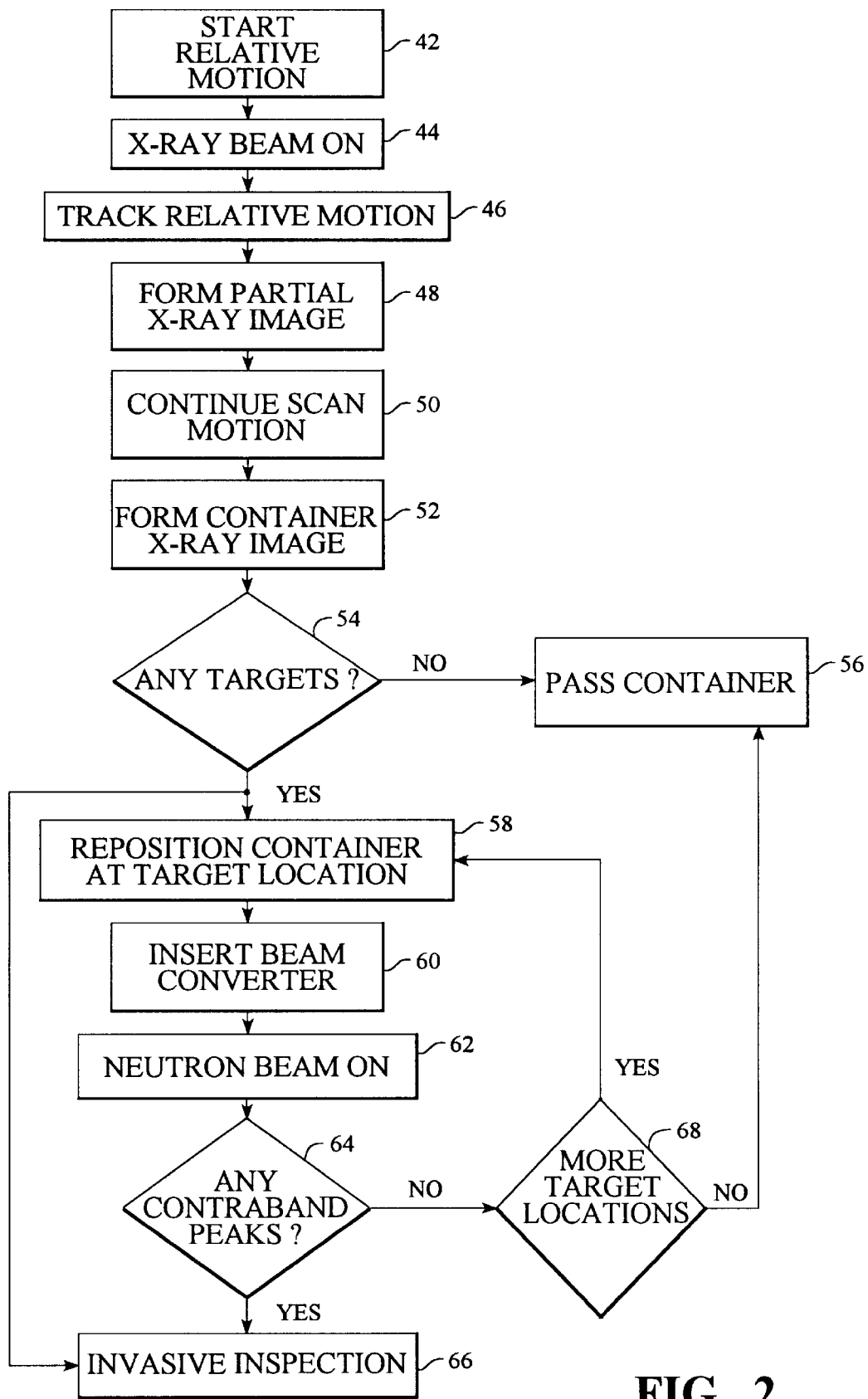
FIG. 2 is a diagram showing a sequence of operations for the system of FIG. 1.

With reference to FIG. 2, an on-off switch which is part of the target acquisition search electronics initiates motion by a signal to the motion controller. The start of relative motion is indicated in block 42. As soon as the leading edge of the container passes in front of the sensor, the X-ray beam is turned on, indicated by block 44. Relative motion between the container and the beam position is carefully measured by sensors so that the container can be moved back to a desired location, if desired. Block 46 indicates tracking of relative motion, for example, by electrooptical position sensors. In such a system, a long decal, having markings similar to a roller is adhered to the side of the container. An optical transmitter and receiver count marks to measure the advancement of the container from a home or start position. An alternative would be to attach a motion encoder to the motion control device 32 to measure motion. Relative position of the container relative to the beam and detector array is important because the image processing electronics are forming an X-ray image from data received in the detector array. The formation of a partial X-ray image is indicated by block 48. The container can be moved back and forth continuing the scan motion, indicated by block 50 until the entire X-ray image is formed, indicated by block 52. With a complete X-ray image of the container present, there is an inquiry either by the image analyst or by a computer associated with target acquisition electronics regarding whether end targets are seen. This is indicated by decision block 54. If no targets are seen, the container is passed, indicated by decision block 56. If a target or likely target is identified, the motion system repositions the container in front of the X-ray beam at the target location, indicated by block 58. At this point, neutron probing of the target or suspected target occurs by insertion of the beam converter plate in front of the X-ray beam, indicated by block 60. This results in creation of a neutron beam, indicated by block 62 which enters the container, with neutron absorption occurring for several elemental species. Some of the species are identified with contraband. Characteristic gamma rays are given off, with energies which are unique to specific elements. Such elements are indicators of contraband and a decision is made in the decision block 64 whether energy peaks indicative of contraband exists. If so, the container is invasively inspected, indicated by block 66. If no contraband peaks are seen, there is an inquiry at decision block 68 whether any more target locations exist. If not, the container is passed. If so, the container is repositioned at the next target location.

Figure 3:
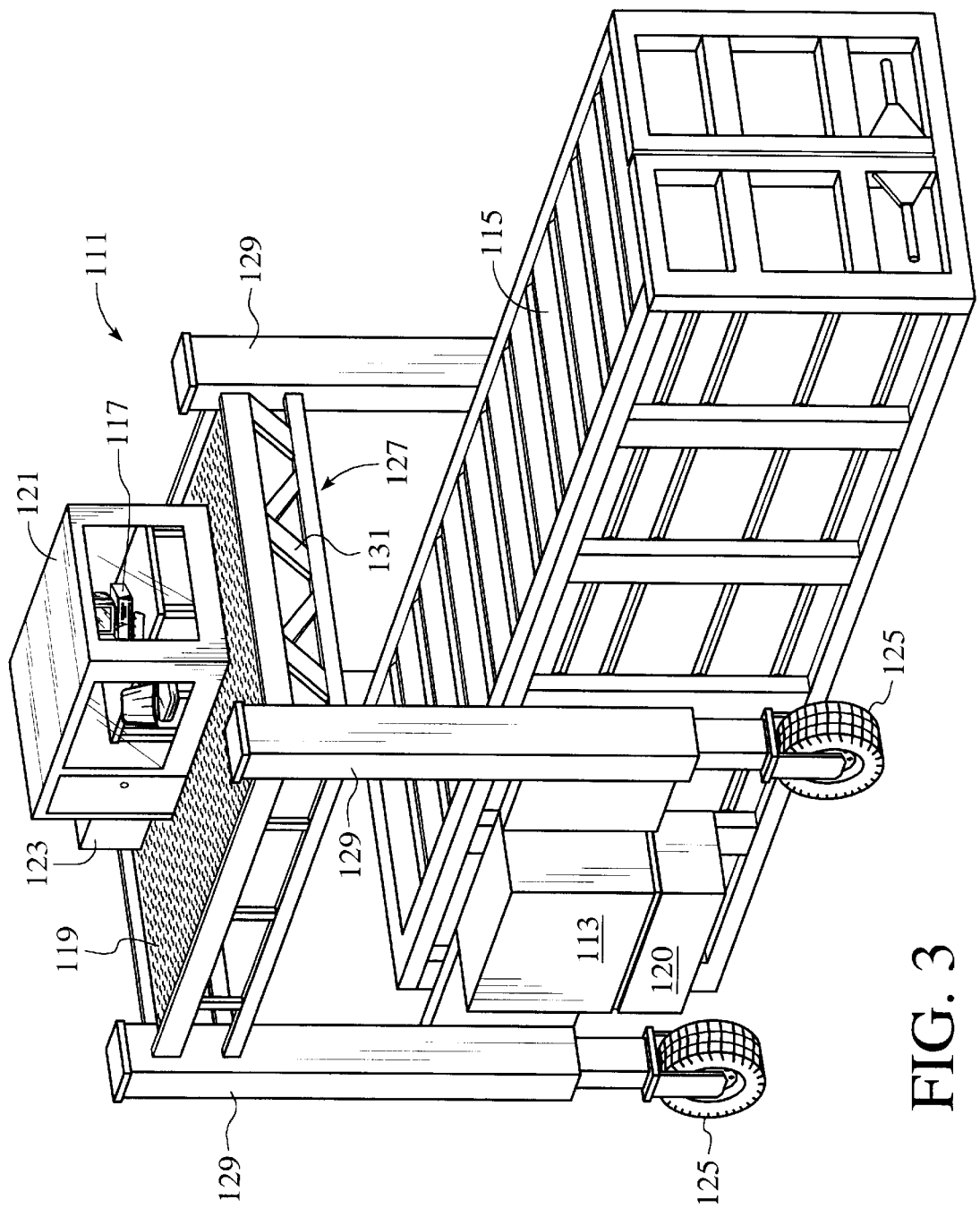
FIG. 3 is a perspective view of a second embodiment of the system of FIG. 1, with a movable inspection station and a stationary container.

For some situations where containers are stationary, a mobile inspection system is used, following the teachings of my prior application, now U.S. Pat. No. 5,638,420. With reference to FIG. 3, the straddle carrier vehicle 111 serves as the support structure for an X-ray source 113 of the linac type discussed above; a detector array, not seen on the opposite side of container 115; gamma-ray detectors with additional detectors located above or on the far side of the container 115; the associated computer and image display system 117; shielding platform 119 for supporting and protecting the operator/analyst and for general operational safety; the operator/analyst room 121; and for associated power supplies, air conditioning equipment, power generating equipment, and radiation sensors, all contained in housing 123. A beam converter plate, not shown, may be selectively interposed in front of the X-ray beam to generate a neutron beam.

The straddle carrier vehicle 111 has an engine under shielding platform 119, not seen, to enable movement under its own power to other locations within an inspection area or to other inspection areas. The vehicle's movement also provides the relative motion between the X-ray beam source 113 and detectors, held fixed with respect to each other, on the one hand, and the container 115 or vehicle being inspected on the other hand, enabling an image to be formed of the object being inspected as the straddle vehicle passes over the object, thereby continuously illuminating the object by a beam of X rays which is collimated for sharpness.

The straddle carrier vehicle 111 may be of the type currently used at seaports to move ocean-going shipping containers. Manufacturers of such straddle carriers include Shuttlelift, Noell and others. The main difference between the straddle carrier vehicle 111 of this invention and the commercial units of the prior art is that there will not be a container "spreader" or "hoist" in the present invention. Instead, an X-ray beam source housing 113 and a detector mounting housing are disposed across opposed legs 129. Platform 119 with supporting shielding, the operator/analyst cab 121, and the previously mentioned ancillary equipment are added to the top of the vehicle.

The straddle carrier vehicle is seen to have four wheels 125; a heavy-duty, rigid structural steel, inverted U-shaped frame 127; travel warning alarms; an industrial engine, either gasoline or diesel; and all controls required for operation. The inverted U-shaped frame 127 may have telescoping legs 129 and cross beams 131. If employed, the telescoping legs 129 extend so that the straddle carrier is able to straddle two stacked containers with X-ray beam source 113 of the type previously described with beam flux and energy sufficiently high to direct a beam to traverse the space through a container to detectors at the other side. The U-shaped frame 127 is U-shaped both in the longitudinal direction as well as in the crosswise direction. The cross beam 131 and similar peripheral beams supporting radiation shielding platform 119 should be braced to carry additional shielding where intense sources are used. Such intense sources may be linear accelerators producing electron beams which bombard a target, usually a metal film, emitting X rays. The choice of source type and its intensity and energy depends upon the sensitivity of the detectors, the radiographic density of the cargo in the space between the source and detectors; radiation safety considerations; and operational requirements, such as the inspection speed.

An alternative control system may be employed, particularly if the radiation safety of the operator/analyst or the weight of the shielding, etc. become issues. A remote operational feature is presently available on commercial straddle carriers permitting full operation of the vehicle from up to 200 yards away, with radio or cable transmission of control signals. This may eliminate the cab 121, display, and some of the controls from the straddle carrier, reducing the shielding and power consumption. In this case, the image data could be recorded digitally or transmitted for analysis at a different location.

In scanning a container, a new inspection method is used. A straddle carrier moves relative to a fixed container making one or more passes back and forth over the length of the container. The source and detector array are moved along the length of the container, continually recording the radiographic transmission image as the collimated radiation beam is swept along the container. For the detection of cars in a container, the source and detector position are fixed in height. However, for other inspection objectives, the height of the source and detector may need to be adjusted in elevation so that in one pass, a first elevation is scanned and then on another pass, a different elevation is scanned. In many instances, a single pass will be sufficient to form an X-ray image, but to probe suspicious areas found in the X-ray image from a single pass, the straddle carrier must be moved so as to position the X-ray beam at the suspicious areas and a converter put in place to create photoneutrons so that the suspicious areas can be subjected to photoneutron probing.

Figure 4:
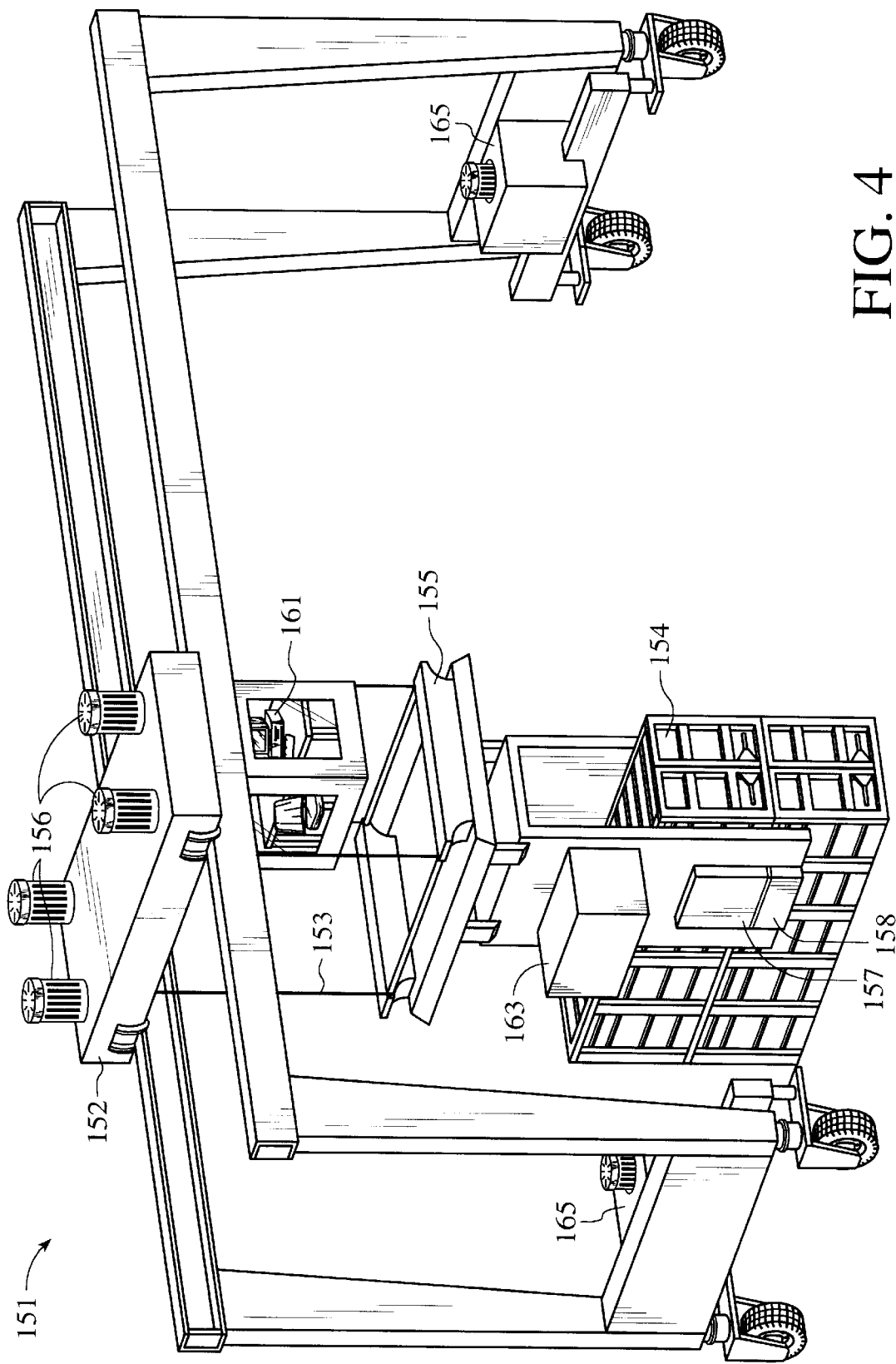
FIG. 4 is a perspective view of another version of the second embodiment, shown in FIG. 3.

An alternative to the straddle vehicle would be any other type of movable conveyance that provides the requisite support for the source, detector array and ancillary apparatus; enables the source and detector to be held in alignment; and enables the source and detector to be passed at a uniform speed simultaneously on opposite sides of the container or vehicle being inspected. In particular, a straddle crane 151, shown in FIG. 4, uses a robotic gripper 155 and a connecting cable system 153, supported from rail-mounted carriage 152, to maintain the spaced-apart alignment of the X-ray linac source 157 and a detector array, not seen behind container 154. A gamma-ray detector 158 is positioned below the X-ray source 157 to detect gamma rays associated with contraband. Cable system 153 is raised and lowered by motors 156 in response to commands from the operator/analyst room 161. Associated power supplies, air conditioning equipment and radiation sensors are mounted in housing 163. Wheel and steering power engines or motors are mounted in housings 165. There are cranes of this general type in common use at ports designated as "straddle cranes" or "straddle lifts". In some instances, it may be desirable to operate the straddle vehicle or crane along a fixed route using wheel guides or mounted on rails.

A way to enhance X-ray images made by a moving source and detector has been found. In one embodiment, the motion of the straddle vehicle as it passes over and alongside the object being inspected is made steady and with constant velocity. Any irregularities in the motion of the straddle vehicle will result in distortions in the image, and so in the first embodiment motion is made as regular, even and constant as feasible using known control systems. For the detection of large contraband, such as stolen cars hidden within international shipping containers, only coarse spatial resolution in the image is required, i.e. approximately one inch. In such cases, it may be sufficient to control the motion procedurally, i.e., by bringing the straddle vehicle to approximately a constant speed with a speed controller, i.e, "cruise control", prior to passing over the container or rail car being inspected and by maintaining that speed as accurately as possible using the straddle vehicle's throttle.

In a second embodiment, irregularities of motion are measured and the radiographic image is correspondingly corrected. To accomplish this, one or more motion encoders can be affixed to one wheel of the straddle vehicle. For example, an encoder measures the rotational velocity of the wheel and transmits a corresponding electrical signal to the imaging system's computer. Wheel encoders are sometimes known as shaft angle encoders. If there is a change in speed, the computer automatically includes a corresponding compensation in the timing of the detector signals for that location, thereby eliminating nonuniform-motion-induced image distortions. As an alternative to the wheel encoder, a linear strip bearing evenly spaced bars can be attached to the side of each container using magnetic attachment, tape or other suitable means. During the imaging procedure, the strip can be "read" by one of several commercially available detectors. The linear strip and detector form an optical encoder producing a signal from the reflected or scattered light that can be used to correct the image data for motion-induced irregularities. Vertical as well as horizontal motion can be measured. In addition to linear translation encoding, for some applications it may be desirable to encode other system motions, such as the pitch and yaw of the vehicle.

I claim:

1. A security inspection apparatus for probing the contents of a cargo container comprising,
    an X-ray source having an output beam with sufficient energy and flux for traversing a cargo container,
    X-ray detectors disposed to intercept the output beam of the X-ray source after traversing the cargo container, the detector having an output signal,
    a motor connected to the X-ray source and X-ray detectors in a position establishing relative motion, in a scan pattern, between the cargo container on the one hand and the source and detector on the other hand,
    a beam recorder connected to receive the output signal from the detectors and plot a representation of the cargo container,
    a beam converter selectively movable into the X-ray beam path between the X-ray source and the cargo container capable of converting the X-ray beam into a neutron beam directed into the cargo container,
    a gamma radiation spectrometer capable of detecting gamma rays from neutron activation of specific atoms, said spectrometer disposed in proximity to the cargo container and producing a signal in response to said gamma rays.

2. The apparatus of claim 1 wherein the X-ray source comprises a linear accelerator having an output energy of at least 1.67 MeV.

3. The apparatus of claim 1 wherein the X-ray source comprises a pulsed source.

4. The apparatus of claim 1 wherein the X-ray detector comprises a stack of detectors or cells.

5. The apparatus of claim 1 wherein the beam recorder comprises semiconductor memory storing density data from the detector cells.

6. The apparatus of claim 5 wherein the beam recorder further comprises a computer with image processing software means for assembling the representation of the contents of the cargo container from density data in the semiconductor memory.

7. The apparatus of claim 1 wherein the beam converter is a beryllium plate.

8. The apparatus of claim 1 wherein the motor is associated with motion control electronics which moves the cargo container back and forth past the X-ray beam until most of the cargo container passes before the X-ray output beam.

9. The apparatus of claim 8 wherein the motion control electronics has associated position sensors allowing bringing the cargo container before the output beam at locations wherein contraband has been identified.

10. The apparatus of claim 1 wherein said motor is associated with a straddle vehicle.

11. A security inspection apparatus for containers comprising:
    a support apparatus in proximity to at least one container to be inspected,
    an X-ray source generating an X-ray beam mounted on said support apparatus, said X-ray beam having an energy and flux capable of traversing said container,
    an X-ray beam density detector disposed to intercept the X-ray beam penetrating said container,
    means for providing relative motion between the X-ray beam and the container to the extent of scanning at least most of the container, motion tracking detectors associated with the means for providing relative motion having connected memory means for recording positions of the X-ray beam relative to the container, an X-ray beam-to-neutron beam converter selectively movable into the X-ray beam path, the neutron beam having energy and flux for penetrating said container causing neutron activation of target substances in the container, a gamma-ray energy detector disposed in the vicinity of the container to sample gamma rays from neutron activation of the target substances, whereby an X-ray beam serves to image containers for targets and to identify the targets for probing with neutron to activate characteristic radiation.

12. The security inspection apparatus of claim 11 wherein the support apparatus is mobile.

13. The security inspection apparatus of claim 12 wherein the support apparatus is a straddle carrier vehicle.

14. The security inspection apparatus of claim 12 wherein the support apparatus is a straddle crane vehicle.

15. The security inspection apparatus of claim 11 wherein the support apparatus is fixed.

* * * * *